United States Patent [19]

Bennett et al.

[11] Patent Number: 4,554,266

[45] Date of Patent: Nov. 19, 1985

[54] COPPER-MAGNESIUM CATALYST AND METHOD FOR ALKYLATION OF HYDROXYAROMATIC COMPOUNDS THEREWITH

[75] Inventors: James G. Bennett, Glenmont; Gregory R. Chambers, Delmar, both of N.Y.

[73] Assignee: General Electric Company, Schenectady, N.Y.

[21] Appl. No.: 500,683

[22] Filed: Jun. 3, 1983

[51] Int. Cl.$^4$ .................... B01J 23/00; C07C 37/16
[52] U.S. Cl. .................... 502/344; 502/344; 502/345; 568/794; 568/804
[58] Field of Search ........... 568/794, 804; 502/340, 502/344, 345

[56] References Cited

U.S. PATENT DOCUMENTS

| | | | |
|---|---|---|---|
| 1,500,794 | 7/1924 | Bouvier et al. | 502/340 |
| 1,913,774 | 6/1933 | Seib | 502/340 |
| 2,524,566 | 10/1950 | Houtman et al. | 502/340 |
| 3,304,268 | 2/1967 | Lester et al. | 502/340 |
| 3,446,856 | 4/1969 | Hamilton | 568/804 |
| 3,968,172 | 7/1976 | Ichikawa et al. | 568/804 |
| 4,085,150 | 4/1978 | Smith | 568/804 |
| 4,201,880 | 7/1980 | van Sorge | 568/804 |
| 4,208,537 | 6/1980 | Kawamata et al. | 568/794 |

FOREIGN PATENT DOCUMENTS

| | | | |
|---|---|---|---|
| 6927367 | 4/1967 | Japan | 568/804 |
| 0035061 | 9/1978 | Japan | 568/804 |
| 0040430 | 3/1982 | Japan | 502/340 |
| 0070839 | 4/1983 | Japan | 502/340 |
| 1398560 | 6/1975 | United Kingdom | 568/804 |
| 0697179 | 11/1979 | U.S.S.R. | 502/340 |

OTHER PUBLICATIONS

*Chem. Abstracts,* 80, 120534a (1974).

*Primary Examiner*—Werren B. Lone
*Attorney, Agent, or Firm*—William H. Pittman; James C. Davis, Jr.; James Magee, Jr.

[57] ABSTRACT

Hydroxyaromatic compounds such as phenol are alkylated with alkanols such as methanol in the presence of a catalyst comprising an intimate blend of magnesium oxide and copper, the latter being present in an amount up to about 2% by weight, based on said magnesium oxide. The catalyst is prepared by blending a magnesium reagent and copper in elemental or (preferably) chemically combined form and calcining the same at a temperature within the range of about 350°–550° C. The catalyst promotes ortho-alkylation of the hydroxyaromatic compound in high yield, minimizes decomposition of the alkanol, and has long life.

29 Claims, No Drawings

COPPER-MAGNESIUM CATALYST AND METHOD FOR ALKYLATION OF HYDROXYAROMATIC COMPOUNDS THEREWITH

This invention relates to new catalyst compositions and methods for their preparation and use, and more particularly to catalysts having improved selectivity for ortho-alkylation of hydroxyaromatic compounds with alkanols and resulting in decreased by-product formation during said alkylation.

Ortho-alkylated hydroxyaromatic compounds are known to be useful for various purposes. For example, 2-alkyl- and 2,6-dialkylphenols may be oxidatively coupled to yield polyphenylene oxides, some of which are used as constituents of engineering plastics.

A typical method for preparation of such compounds is by alkylation of the precursor hydroxyaromatic compound with a primary or secondary alkanol in the presence of a suitable catalyst. The use of magnesium oxide catalysts for this purpose is disclosed in U.S. Pat. Nos. 3,446,856 and 4,201,880. According to Japanese Kokai 69/27367, the selectivity of such catalysts for o-alkylation is improved by combining them with 0.5–50% by weight of copper or a similar metal.

Notwithstanding the above-identified disclosures, various problems still exist with the alkylation methods and the catalysts used therein. In the first place, the active life of many of these catalysts is undesirably short, sometimes less than 50 hours.

In the second place, many of such methods and catalysts still produce an undesirably high proportion of p-alkylated products of marginal utility. Thus, alkylation of phenol with methanol in the presence of magnesium oxide yields o-cresol and 2,6-xylenol, the desired products, but in addition yields substantial amounts of such p-substituted compounds as p-cresol, 2,4-xylenol and mesitol (2,4,6-trimethylphenol). These p-substituted compounds are much less useful than the corresponding compounds containing unsubstituted para positions, since they do not yield polymers with the desirable properties possessed by the polyphenylene oxides prepared from such compounds as 2,6-xylenol.

In the third place, the high temperatures (above 460° C. and frequently about 500° C.) required for alkylation using previously known catalysts require an undesirably high energy input and decrease catalyst life. In addition, such temperatures introduce other problems such as thermal decomposition of the reactants. For example, methanol is dehydrogenated under alkylation conditions to formaldehyde, a desirable reaction since the aldehyde is a necessary alkylation intermediate. However, at extremely high temperatures a substantial amount of formaldehyde decomposes to carbon monoxide and hydrogen. Such decomposition products are of little use except as fuel. It is strongly preferred to minimize decomposition of methanol and formaldehyde so as to enable their use for alkylation.

A principal object of the present invention, therefore, is to produce novel catalysts useful for alkylation of hydroxyaromatic compounds.

A further object is to produce catalysts with long life and a high degree of selectivity for ortho-alkylation.

A further object is to provide catalysts which minimize loss of alkanol and high energy usage in the alkylation process.

A further object is to provide an improved process for the ortho-alkylation of hydroxyaromatic compounds with alkanols.

A still further object is to optimize alkanol usage during said alkylation.

Other objects will in part be obvious and will in part appear hereinafter.

The above objects are attained according to the present invention by providing a method for preparing a solid catalyst composition which comprises intimately blending (1) a magnesium reagent which yields magnesium oxide upon calcination with (2) copper in elemental or chemically combined form and calcining the resulting blend at a temperature within the range of about 350°–550° C., the amounts of said basic magnesium reagent and copper being such that the calcined product contains up to about 2% copper by weight based on magnesium oxide.

Any magnesium reagent which yields magnesium oxide upon calcination may be used in the catalyst preparation method of this invention. Illustrative reagents are magnesium oxide, magnesium hydroxide, magnesium carbonate and mixtures thereof. Magnesium oxide exists in an inactive "dead burned" and a "reactive" form; the reactive form is the one which is suitable for use according to this invention. Particularly useful as a magnesium reagent is basic magnesium carbonate, which is a commercially available material. It is also known as magnesium carbonate hydroxide and is identified in The Merck Index, Ninth Edition, in monograph #5483 as having the approximate formula $(MgCO_3)_4 \cdot Mg(OH)_2 \cdot 5H_2O$.

The copper constituent used in the preparation of the catalysts of this invention may be elemental or chemically combined copper. It is preferably chemically combined, since surface area may then be easily maximized for optimum catalytic effect. Both cuprous and cupric compounds are suitable; catalysts prepared from cuprous compounds frequently exhibit superior activity, and the use of cuprous compounds is therefore especially preferred. Illustrative copper compounds which may be used are cuprous oxide, cuprous chloride, cupric oxide, cupric sulfate, cupric chloride and cupric nitrate. Also included are coordination complexes of copper, exemplified by the complexes with ammonia and amines.

According to this invention, an intimate blend of the magnesium reagent and copper is prepared. This may be and is frequently preferably effected by merely blending the dry reagents in particulate form. Alternatively, an aqueous slurry of the reagents may be prepared and the water removed therefrom by filtration, centrifugation or the like. If the slurry method is used the magnesium reagent and copper constituent should be substantially insoluble in water to avoid loss upon water removal, and the blend should be dried, usually by heating at a temperature up to about 200° C., typically in a vacuum oven.

The relative proportions of copper and magnesium reagent are adjusted to provide a calcined product containing up to about 2% copper by weight based on magnesium oxide. Preferably the catalyst will contain at least about 0.25% and most desirably about 0.5–1.25% copper.

For the sake of convenience of storage and use, it is frequently preferred to pelletize the blend before calcining. This is ordinarily effected by sieving (typically through a 25 mesh sieve), milling and compressing. To facilitate pelletizing, binders, fillers and/or pelletizing lubricants known in the art (hereinafter collectively designated "fillers") may be incorporated into the catalyst. Typical of these are graphite and polyphenylene oxide. The filler content of the pelletized solid may be up to about 25% and preferably below about 10% by weight, based on copper plus magnesium oxide, depending on the filler used; polyphenylene oxide is most often used in an amount up to about 10%, and graphite in an amount up to about 5%.

The solid blend is then calcined by heating at a temperature within the range of about 350°–550° C. During calcination, the magnesium reagent (if other than magnesium oxide) is converted to magnesium oxide which is the active magnesium species in the catalyst. Calcination temperatures higher than about 550° C. are undesirable since they may result in sintering of the magnesium oxide, with a decrease in surface area and consequently in catalyst activity.

The active copper species in the catalyst is believed to be elemental copper. Therefore, it is important to reduce combined copper in the solids to the elemental state. Reduction may be effected before, during or after calcination, and the conditions of calcination determined accordingly. Thus the calcination atmosphere may be oxidizing (e.g., oxygen or air), inert (e.g., nitrogen) or reducing (e.g., hydrogen or other reducing agents). The presence of substances such as water, alkanol and hydroxyaromatic compound is also permissible.

Calcination in a reducing atmosphere is frequently preferred. For example, it may be effected in the presence of hydrogen, typically at about 375°–550° C. It is often most preferred to calcine at about 350°–450° C., preferably about 360°–380° C., in contact with the alkanol-hydroxyaromatic compound feed stream for alkylation. The copper is then reduced by alkanol which is oxidized to the corresponding aldehyde, the essential alkylation intermediate.

The catalysts produced by the method of this invention comprise intimate blends of magnesium oxide and copper in elemental or chemically combined form, the amount of said copper being up to about 2% by weight, preferably at least about 0.25% and most often about 0.5–1.25%, based on said magnesium oxide. Catalyst compositions of this type are also an aspect of the invention.

The preparation of the catalyst compositions of this invention is illustrated by the following examples.

EXAMPLE 1

A slurry of 300 grams of basic magnesium carbonate and 3.03 grams of cuprous oxide in 200 ml. of distilled water was stirred for 1 hour and filtered. The solids were dried in a vacuum oven at 105° C. and put through a 25 mesh sieve. There was added 1.5 grams (0.5% by weight) of graphite and the mixture was precompressed, reground to 25 mesh and pelletized in cylindrical pellets, 3/16 inch in diameter and ⅛ inch long. The tablets were calcined in an alkylation reactor during use by heating from 370° C. to 440° C. in the presence of a phenol-methanol feed (as described in Example 9) to yield the desired catalyst composition which contained 2.1% copper by weight based on magnesium oxide.

EXAMPLE 2

Basic magnesium carbonate, 400 grams, was put through a 25 mesh sieve and milled in a jar mill with 2 grams of cuprous oxide and 2 grams of graphite. The milled blend was precompressed, reground to 25 mesh and pelletized in cyllindrical pellets as in Example 1. The catalyst composition thus obtained contained 1.08% copper by weight based on magnesium oxide.

EXAMPLE 3

Following the procedure of Example 2, a catalyst containing 0.53% copper was prepared.

EXAMPLE 4

The procedure of Example 2 was repeated using cupric oxide instead of cuprous oxide. The resulting catalyst contained 0.96% copper by weight.

EXAMPLE 5

The procedure of Example 2 was repeated, using copper powder instead of cuprous oxide. The resulting catalyst contained 1.2% copper by weight.

EXAMPLES 6–8

The procedure of Example 2 was repeated, except that 8, 20 and 40 grams, respectively, of polyphenylene oxide were added with the graphite.

The hydroxyaromatic compounds which may be alkylated with the catalyst of this invention include all of such compounds which have a free ortho-position. Examples are phenol, 1-naphthol, 2-naphthol, o-cresol, m-cresol, p-cresol, 2,4-xylenol, o-ethylphenol, p-isopropylphenol, p-n-butylphenol, 2,4-diethylphenol, catechol, resorcinol and hydroquinone. In general, any alkyl substituents will be primary or secondary, preferably primary, and will contain up to about 4 carbon atoms. The most preferred hydroxyaromatic compounds are the monohydroxyaromatic compounds and especially those in which the para-position is unsubstituted. Phenol, i.e., monohydroxybenzene, is the preferred hydroxyaromatic compound. o-Cresol, which is a by-product in the methylation of phenol to 2,6-xylenol, is somewhat less preferred. Mixtures of any of these compounds may also be used.

The alkanol used for alkylation may be primary or secondary and is usually primary. It is most often a lower alkanol, that is, one containing up to 7 carbon atoms. Illustrative alkanols are methanol, ethanol, 1-propanol, 2-propanol, 1-butanol, 2-methyl-1-propanol and 1-hexanol. Especially preferred are alkanols containing up to 4 carbon atoms. For reasons of availability, cost and particular utility of the alkylated product, methanol is the most preferred alkanol.

Except when otherwise noted herein, the alkylation conditions used according to this invention are those described in the aforementioned U.S. Pat. Nos. 3,446,856 and 4,201,880, the disclosures of which are incorporated by reference herein. Pressures may vary from atmospheric to as high as about 150 psig. but usually need be no higher than about 30 psig. The proportion of catalyst with respect to reactants in conveniently defined in terms of liquid hourly space velocity (LHSV), which is the volume of liquid feed per unit volume of catalyst per hour, and is typically about 1.5–2.5.

The maximum alkylation temperature employed according to this invention is about 475° C. A typical alkylation temperature range is about 400°–475° C. and preferably about 420°–450° C. For the most part, the temperatures within this range are substantially lower than those disclosed in the aforementioned patents. In addition to decreasing the necessary energy input, the use of these lower temperatures minimizes alkanol wastage.

The utility of the catalysts of this invention in the alkylation of hydroxyaromatic compounds is illustrated by the following examples. All percentages are by weight.

EXAMPLE 9

A reactor was loaded with 110 ml. of the catalyst of Example 1, and heated to 370° C. The reactor was pressurized with nitrogen to 25 psig. and nitrogen was passed through as the temperature was increased to a maximum of 440° C. After 15 minutes, a mixture of 128 grams of methanol, 84 grams of phenol and 44 grams of water (4:1 molar ratio of methanol to phenol) was fed to the reactor at 215 ml./hr. (LHSV of 2.0). The alkylation was run for 502 hours, during which the yields of o-cresol, 2,6-xylenol, p-cresol, 2,4-xylenol and mesitol were monitored and weighted averages calculated. The selectivity of the catalyst, which is defined as the ratio of 2,6-xylenol yield to combined yield of 2,4-xylenol and mesitol, was determined from these average yields. Also measured was off-gas evolution in standard cubic feed per hour (SCFH), which is proportional to the amount of methanol decomposition to carbon-monoxide and hydrogen. The results are given in Table I, compared with Controls 1 and 2 using catalysts prepared by a similar procedure but containing 11.3% and 23.8% copper, respectively.

TABLE I

|  | Control 1 | Control 2 | Ex. 1 |
|---|---|---|---|
| 2,6-Xylenol, % | 69.15 | 67.20 | 73.15 |
| o-Cresol, % | 15.38 | 17.55 | 12.50 |
| p-Cresol, % | 0.04 | 0.03 | 0.04 |
| 2,4-Xylenol, % | 0.63 | 0.62 | 0.59 |
| Mesitol, % | 9.73 | 8.91 | 10.34 |
| Selectivity | 6.67 | 7.05 | 6.69 |
| Off-gas, SCFH | 0.62 | 0.64 | 0.48 |

As the data in Table I show, the results using the catalyst of this invention are about equivalent to those using the controls in percent 2,6-xylenol, percent mesitol and selectivity. However, the off-gas production of the catalyst of this invention was substantially lower than those of the controls.

EXAMPLE 10

The procedure of Example 9 was repeated, except that the alkylation was run for 785 hours using the catalysts of Examples 2 and 5. The control was a magnesium oxide catalyst prepared from basic magnesium carbonate but containing no copper. The results are given in Table II.

TABLE II

|  | Control | Ex. 2 | Ex. 5 |
|---|---|---|---|
| 2,6-Xylenol, % | 56.77 | 65.18 | 60.79 |
| o-Cresol, % | 18.82 | 16.78 | 16.31 |
| p-Cresol, % | 0.04 | 0.05 | 0.01 |
| 2,4-Xylenol, % | 0.66 | 0.65 | 0.51 |
| Mesitol, % | 5.40 | 6.23 | 7.31 |
| Selectivity | 9.37 | 9.46 | 7.77 |
| Off-gas, SCFH | 0.29 | 0.33 | 0.38 |

These results show the increase in yield of the desired 2,6-xylenol using a copper-containing catalyst of the present invention as compared with a catalyst from which copper is absent.

EXAMPLE 11

The procedure of Example 9 was repeated except for differing run times, using the catalysts of Examples 3, 4 and 6–8. The results, including reaction times, are given in Table III.

TABLE III

|  | Ex. 3 | Ex. 4 | Ex. 6 | Ex. 7 | Ex. 8 |
|---|---|---|---|---|---|
| Time, hrs. | 335 | 335 | 486 | 486 | 486 |
| 2,6-Xylenol, % | 64.77 | 69.98 | 71.76 | 66.07 | 60.59 |
| o-Cresol, % | 17.16 | 11.75 | 14.71 | 15.70 | 16.91 |
| p-Cresol, % | 0.22 | 0.05 | 0.09 | 0.13 | 0.15 |
| 2,4-Xylenol, % | 1.34 | 1.11 | 0.67 | 0.77 | 0.79 |
| Mesitol, % | 8.16 | 11.62 | 8.29 | 8.74 | 8.01 |
| Selectivity | 6.82 | 5.49 | 8.01 | 6.95 | 6.89 |
| Off-gas, SCFH | 0.28 | 0.56 | 0.42 | 0.40 | 0.36 |

The results in Table III show that catalysts prepared from cupric salts (Example 4) or containing less copper (Example 3) have properties generally comparable, though sometimes somewhat less desired, than the preferred catalysts. They also show the effects of increasing the proportion of filler in the composition; namely, some decrease in activity which is predictable considering the decreased proportion of active ingredients.

In addition to the previously described advantages, the catalysts of this invention are characterized by long active life, typically remaining active for 800 hours or more of use.

What is claimed is:

1. A method for preparing a solid composition which comprises initially blending (1) a magnesium reagent which yields magnesium oxide upon calcination with (2) copper in elemental or chemically combined form and calcining the resulting blend at a temperature within the range of about 350°–550° C., the amounts of said basic magnesium reagent and copper being such that the calcined product contains about 0.25–2% copper by weight based on magnesium oxide.

2. A method according to claim 1 wherein the copper is in chemically combined form.

3. A method according to claim 2 wherein the magnesium reagent is at least one of magnesium oxide, magnesium hydroxide and magnesium carbonate.

4. A method according to claim 2 wherein the copper content of said blend is such that the calcined product contains about 0.5–1.25% copper by weight.

5. A method according to claim 3 wherein the blend is pelletized before calcining.

6. A method according to claim 4 wherein the pellets additionally contain at least one filler in an amount up to about 25% by weight, based on copper plus magnesium oxide.

7. A method according to claim 4 wherein the filler is at least one of polyphenylene oxide and graphite in an amount up to about 10% and about 5% by weight, respectively.

8. A method according to claim 5 wherein the magnesium reagent is basic magnesium carbonate.

9. A method according to claim 7 wherein calcination is effected by heating in the presence of hydrogen at about 375°–550° C. before catalyst use.

10. A method according to claim 7 wherein calcination is effected by heating at about 350°–450° C. in contact with an alkylation feed stream comprising at least one alkanol and at least one hydroxyaromatic compound.

11. A method according to claim 8 or 9 wherein the copper is provided by cuprous oxide.

12. A catalyst composition prepared by a method according to claim 1, 2, 3, 5, 7 or 11.

13. A catalyst composition comprising an intimate blend of magnesium oxide and copper in elemental or chemically combined form, the amount of said copper being about 0.25–2% by weight based on said magnesium oxide.

14. A composition according to claim 13 wherein the copper content is about 0.5–1.25% by weight.

15. In a method for alkylating at least one hydroxyaromatic compound having a free ortho-position by the catalytic reaction of the same with at least one lower primary or secondary alkanol, the improvement which comprises carrying out said reaction at a temperature within the range of about 400°–475° C. in the presence of the composition of claim 12.

16. A method according to claim 15 wherein the alkanol is methanol.

17. A method according to claim 16 wherein the hydroxyaromatic compound is a monohydroxyaromatic compound in which the para-position is unsubstituted.

18. A method according to claim 17 wherein the hydroxyaromatic compound is phenol or o-cresol.

19. A method according to claim 18 wherein the alkylation temperature is about 420°–450° C.

20. In a method for alkylating at least one hydroxyaromatic compound having a free ortho-position by the catalytic reaction of the same with at least one lower primary or secondary alkanol, the improvement which comprises carrying out said reaction at a temperature within the range of about 400°–475° C. in the presence of the composition of claim 13.

21. A method according to claim 20 wherein the alkanol is methanol.

22. A method according to claim 21 wherein the hydroxyaromatic compound is a monohydroxyaromatic compound in which the para-position is unsubstituted.

23. A method according to claim 22 wherein the hydroxy aromatic compound is phenol or o-cresol.

24. A method according to claim 23 wherein the alkylation temperature is about 420°–450° C.

25. In a method for alkylating at least one hydroxyaromatic compound by the catalytic reaction of the same with at least one primary or secondary alkanol, the improvement which comprises carrying out said reaction at a temperature within the range of about 400°–475° C. in the presence of the composition of claim 14.

26. A method according to claim 25 wherein the alkanol is methanol.

27. A method according to claim 26 wherein the hydroxyaromatic compound is a monohydroxyaromatic compound in which the para-position is unsubstituted.

28. A method according to claim 27 wherein the hydroxyaromatic compound is phenol or o-cresol.

29. A method according to claim 28 wherein the alkylation temperature is about 420°–450° C.

* * * * *